(12) United States Patent
Prater

(10) Patent No.: US 9,046,492 B1
(45) Date of Patent: Jun. 2, 2015

(54) STIMULATED RAMAN NANOSPECTROSCOPY

(71) Applicant: Craig Prater, Santa Barbara, CA (US)

(72) Inventor: Craig Prater, Santa Barbara, CA (US)

(73) Assignee: Anasys Instruments Corp., Santa Barbara, CA (US)

( * ) Notice: Subject to any disclaimer, the term of this patent is extended or adjusted under 35 U.S.C. 154(b) by 123 days.

(21) Appl. No.: 13/668,250

(22) Filed: Nov. 3, 2012

Related U.S. Application Data

(60) Provisional application No. 61/556,423, filed on Nov. 7, 2011.

(51) Int. Cl.
 *G01J 3/44* (2006.01)
 *G01N 21/65* (2006.01)
 *G01N 21/01* (2006.01)

(52) U.S. Cl.
 CPC .............. *G01N 21/658* (2013.01); *G01N 21/01* (2013.01); *G01N 2201/02* (2013.01)

(58) Field of Classification Search
 USPC ............................................... 356/301, 72–73
 See application file for complete search history.

(56) References Cited

U.S. PATENT DOCUMENTS

2005/0279158 A1* 12/2005 Chen ............................... 73/105

\* cited by examiner

*Primary Examiner* — Abdullahi Nur
(74) *Attorney, Agent, or Firm* — Mark Rodgers

(57) ABSTRACT

A method for achieving measurable sample heating in the vicinity of a probe microscope tip using Stimulated Raman Spectroscopy. Two laser sources, preferably in the UV visible or near IR illuminate the sample, preferably in overlapping diffraction limited spots. At least one of the sources is swept through a frequency range such that the difference frequency corresponds to IR spectral regions of interest. Selective Absorption by differing sample materials at the difference frequency causes measurable sample heating detectable by the probe tip related to IR spectral absorption bands. Thus very high spatial resolution IR spectroscopy may be achieved.

31 Claims, 2 Drawing Sheets

STIMULATED RAMAN NANOSPECTROSCOPY

CROSS REFERENCE TO RELATED APPLICATION

This Application claims priority to U.S. Provisional Application 61/556,423 filed Nov. 7, 2011

STATEMENT REGARDING FEDERALLY SPONSORED RESEARCH OR DEVELOPMENT

Not Applicable

BACKGROUND OF THE INVENTION

The Raman effect refers to a situation where a sample is illuminated with one wavelength of light and a portion of the light is inelastically scattered, i.e. photons are emitted with a different wavelength than the incident photons. The Raman process occurs when the sample can absorb or emit a photon corresponding to the difference in energy between the incident and scattered beam. Spectroscopic measurements can be performed by measuring the amount of light scattered as a function of the difference in energy between the incident and scattered photons. This energy shift, the "Raman shift" is usually reported in wavenumbers (cm-1) that is the reciprocal of wavelength. Plotting the amplitude of scattered light versus the Raman shift allows the generation of vibrational spectra of materials. The positions of peaks in the Raman spectra can provide information about the structural, chemical and electronic properties of a sample.

Conventional Raman spectroscopy is a technique where a sample is illuminated by a pump beam and spectroscopic information about the sample is obtained by measuring wavelength-shifted light scattered from the sample. The scattered light may be at lower energy (Stokes shift) or higher energy (Anti-Stokes). Raman scattering can occur when a vibrational resonance in a sample can absorb or emit energy corresponding to the difference in frequency between the pump beam and the Raman scattered beam. In conventional Raman spectroscopy, the scattered beam is measured spectroscopically to determine the amount of scattered light as a function of between the pump beam and the scattered beam. Conventional Raman spectroscopy has been growing dramatically in recent years because of the rich information that can be obtained about molecular and electronic resonances in a wide variety of materials. It has also been growing relative to infrared spectroscopy as it has superior spatial resolution due to the smaller spot size attainable with visible, UV, or near IR wavelength illumination sources.

Raman spectroscopy does have some limitations, however. First, the Raman effect is often very weak. For example, most photons are scattered by the sample with no wavelength shift and roughly only 1 photon in $10^7$ are shifted. Thus it is necessary to measure a small fraction of Raman shifted photons against a large background. This has led to the use of high power lasers that can easily damage samples. The Raman effect can also be obscured by sample fluorescence, another mechanism that products wavelength shifted photons. Finally, the spatial resolution is also still much coarser than that of a high-resolution technique such as probe microscopes. While some suppliers and publications claim better numbers, practical resolutions obtained by the typical user are around 1 µm or worse.

A variety of techniques have been developed to overcome the spatial resolution limit and increase signal strength. Many of these techniques rely on achieving plasmon amplification around a nanostructure. Such techniques are part of the reason that Raman Spectroscopy is currently in a growth mode, as nanotechnology tools are incorporated to improve Raman detection. One such technique, related to probe microscopy is called Tip-Enhanced Raman Spectroscopy. This technique illuminates a sample with a pump beam in the UV, visible, or near infrared and then detects wavelength shifted photons. This illumination takes place at the tip of a probe microscope, and the tip provides electrostatic ("lightning rod effect" and/or plasmon amplification at its apex. If the amplification is sufficient, a measurement of the Raman effect only in the vicinity of the tip can be separated from the background. The TERS effect has shown substantial promise in some key laboratories, but has not yet to be broadly adopted due to difficulties in reliably obtaining large enhancement factors and high spatial resolution.

Stimulated Raman

Stimulated Raman is a two photon technique that is used to enhance the sensitivity of conventional Raman spectroscopy and microscopy to measure and map Raman absorption bands in the mid-infrared. The basic concept is that two coherent laser beams at different wavelengths (or equivalently, two different optical frequencies) are incident on the same region of a sample. These two beams, called the pump beam and the Stokes beam, respectively, are arranged such that the difference in photon energies of the two beams can probe molecular vibrations in a sample under study. More specifically, the difference between the photon energies can be adjusted to sweep through and excite various molecular resonances. For example if the pump beam has an optical frequency of $\sigma_1$ and the Stokes beam has a frequency $\sigma_2$ energy can be efficiently absorbed by the sample with the difference frequency $\Delta\sigma = \sigma_1 - \sigma_2$, corresponding to a molecular resonances of the sample. The molecular resonance are traditionally detected by measuring the amount of light transmitted, reflected, and/or scattered by a sample using an optical detector in the far field. Measuring the amount of light scattered by a sample as a function of the frequency difference between the two beams, a Raman absorption spectrum of a sample can be created.

Stimulated Raman achieves a significant enhancement over spontaneous Raman by combining the Raman effect with stimulated emission.

Stimulated Raman scattering generates dramatic enhancement in the intensity of the scattered Stokes beam versus spontaneous Raman scattering. The enhancement comes from the pump beam producing a large population of oscillators in an excited state and the Stokes beam enhancing the probability of the excited states decaying through emission of a photon at the Stokes frequency. (This effect is analogous to the stimulated emission and amplification that occurs in a laser.) The net effect is that the probability of emission of a Stokes photon can be dramatically increased versus spontaneous Raman. Gains of order $10^7$ or more can be achieved allowing for efficient Raman imaging. At the same time, this mechanism also dramatically increases the likelihood of absorption of mid-IR photons at the difference wavenumber $\Delta\sigma = \sigma_1 - \sigma_2$, where $\sigma_1$ and $\sigma_2$ are the wavenumbers of the pump and stokes beams. The stimulated Raman effect has been used for dramatic results recently in optical microscopy, for example real-time video imaging of biological samples by the Xie group at Harvard.

AFM-Based Stimulated Raman

A paper was published recently by I. Rajapaksa, and H. Kumar Wickramasinghe called "Raman Spectroscopy and Microscopy Based on Mechanical Force Detection." This paper uses two narrowly tunable CW laser diodes in combination with a heterodyne detection techniques to create a tip-sample force that is proportional to the Raman absorption cross section of a material. The authors demonstrated the ability to obtain spectra over a narrow frequency region in the mid-infrared using two narrowly tunable diode lasers operating in the visible. The mechanism of detection is related to measuring the induced force between the tip and sample from polarization force originating from the electric fields of the incident laser beams interacting with the tip and sample. This paper showed the ability to obtain Raman spectra over a narrow region of the mid-IR and the ability to obtain force-based Raman contrast from individual Raman active molecules. Because of the nature of the sources used, and the experimental set-up, the Authors avoided any significant heating of the sample and restricted their measurements to force interactions due to electromagnetic effects.

Stimulated Raman Photoacoustic Imaging

Recent papers by the Scully group have stimulated Raman spectroscopy using an ultrasonic sensor to measure acoustic waves resulting from the absorption of pulses of Raman photons. They demonstrate spatially resolved stimulated Raman imaging with spatial resolution on the scale of 50-100 um. The acoustic waves are generated due to the absorption of IR energy in the Stimulated Raman process that leads to heating and rapid thermal expansion of the sample. As shown in U.S. Pat. No. 8,001,830, its CIP U.S. application Ser. No. 12/315,859, and other family members, all of which are incorporated by reference, the atomic force microscope can be used to measure and map rapid sample expansion due to optical absorption and sample heating. This technique and its variants is called Photo-Thermal IR Spectroscopy, or PTIR. The PTIR technique has a significant advantage over other photoacoustic techniques since it allows mapping of optical absorption induced thermal expansion on the nanoscale. While conventional photoacoustic techniques have spatial resolution that is fundamentally limited by optical diffraction (and in practice often much coarses), the AFM-based PTIR technique can use the tip of the AFM to measure thermal expansion on lateral scales far below the diffraction limit. Alternately, temperature sensing AFM probes (for example thermocouple or thermistor probes) can directly measure the temperature increase in the vicinity of the probe tip.

No technique, however, has provided robust, high resolution Raman spectroscopy over a wide range of Raman frequencies with spatial resolution consistently on the sub-micron scale.

SUMMARY OF THE INVENTION

The current invention is directed towards providing high resolution, high sensitivity Raman spectroscopy and Raman imaging using the probe microscope (typically and AFM or similar device) with coverage over a broad portion of the mid-IR wavelengths. This is accomplished by illuminating a sample with two laser beams that overlap in space and time. The beams are arranged to have a difference in frequency $\Delta\sigma$ that can be swept over Raman absorption frequencies in the mid-IR. Laser sources and equipment set-up are configured to achieve significant absorption at the difference frequency, leading to measurable sample heating and expansion, which is measured by the probe microscope.

DETAILED DESCRIPTION OF THE INVENTION

Figure 1:
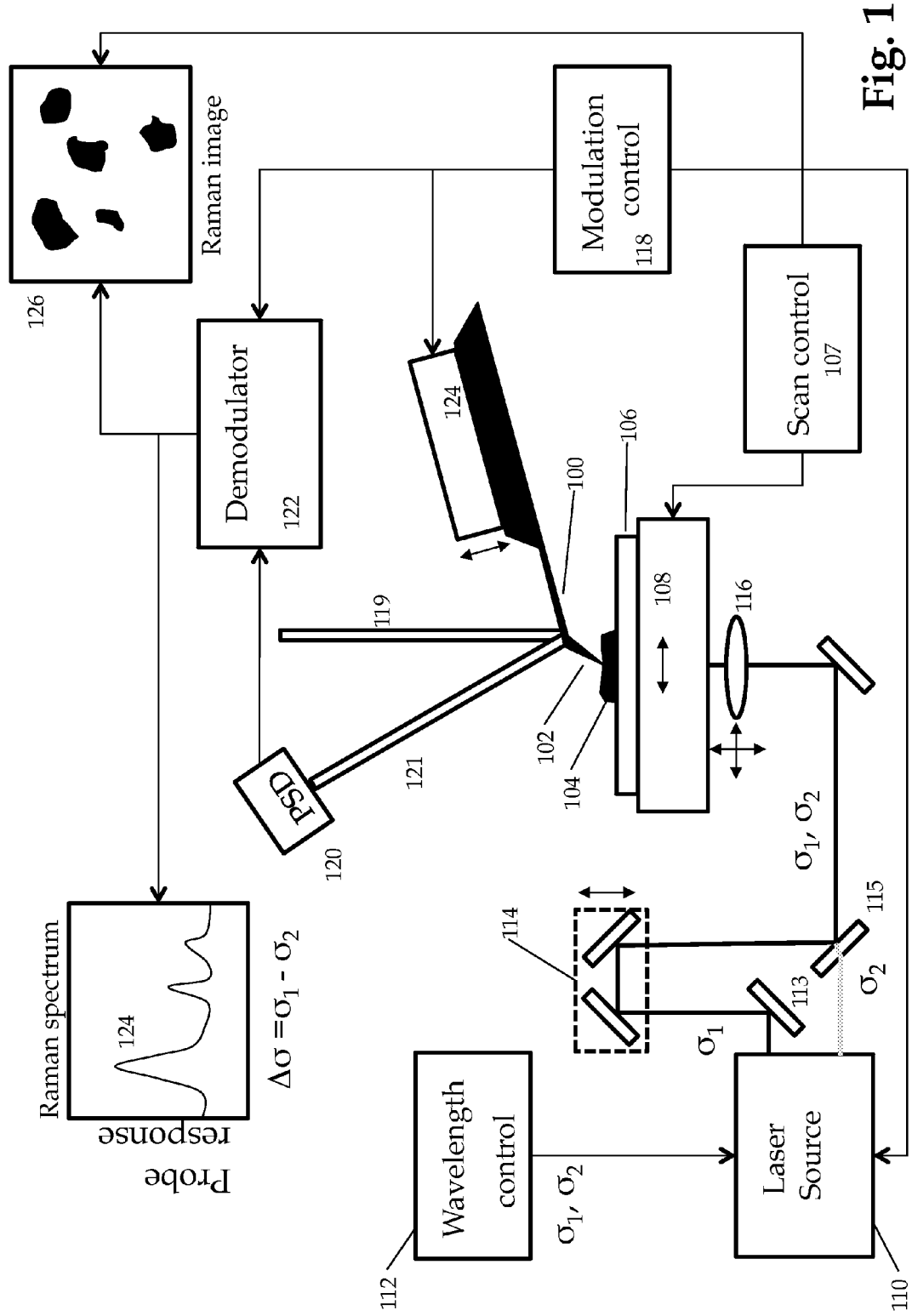
FIG. 1 depicts the integration of a suitable Stimulated Raman Spectrometer with a probe microscope.

FIG. 1 shows a simplified schematic diagram of one embodiment of the current invention. An atomic force microscope cantilever probe 100 with a tip 102 is interacted with a sample 104, optionally on a support substrate 106. The tip may be interacted with the sample in contact mode, intermitted contact mode and/or non-contact mode. A probe modulator 124 can provide an oscillating signal to drive the cantilever into oscillator at one or more frequencies as supplied by modulation control 118. The modulation may include multiple modulation schemes described in copending application Multiple Modulation Heterodyne Force Microscopy U.S. Application Ser. No. 61/460,666 which is incorporated by reference. A laser source 110, or alternatively multiple sources, outputs at least two laser beams at frequencies $\sigma_1$ and $\sigma_2$.

In one embodiment the two beams at frequencies $\sigma_1$ and $\sigma_2$ are aligned to be substantially collinear using one or more beam steering devices shown schematically as mirror 114 and beam splitters 115. In practice multiple adjustable mirrors may be employed to provide sufficient degrees of freedom to align the propagation axes of the two beams. Mirrors or beam splitters on one or both paths may be electronically adjustable to enable automatic adjustment and/or dynamic alignment of the two beams.

The combined beams are focused on a region of the sample in the vicinity of the probe tip 102 using focus mechanism 116. Focus mechanism 116 is shown schematically as a single lens, but it may comprise any suitable focusing element or elements including lenses and/or curved mirrors or any other collection of optics to produce a focused spot. In a preferred embodiment the focus mechanism is a high numerical aperture UV compatible objective. In another embodiment the focus mechanism is an off-axis parabolic mirror. In a preferred embodiment the focus mechanism should be able to provide a diffraction limited or near diffraction limited focused spot. The focus mechanism can optionally include the ability to adjust the position of the focused spots in one or more axes. For example it may include the capability to adjust the vertical focus to optimize the size of the focused spot in the vicinity of the probe tip 102. It may also be used to focus the laser spots at a position below the sample surface. The focus mechanism may also optionally include the ability to translate the focused spots laterally to enable alignment of the laser beams with the probe tip 102. Such translation may for beam alignment may be provide separate from the focus mechanism. Alternately, the probe 100 can be translated instead relative to the laser beams.

In a preferred embodiment the laser source may be a pulsed source. Since the intent of the invention is to achieve rapid detectable sample heating such as described in the PTIR applications, a pulses source is suitable both because of the higher short duration power obtainable and due to the repetitive shock effect leading to decaying contact resonances. In one embodiment the pulse laser source may have a pulse duration of greater than 1 picosecond and in another embodiment a pulse duration of greater than 1 nanosecond. For the stimulated Raman mechanism to work, the pulses from the two beams at $\sigma_1$ and $\sigma_2$ must have at least a partial temporal overlap at the sample. That is their time of arrival at the sample must overlap so that the Stokes beam can enhance the emission at the Raman shifted frequency. For this reason one or more of the beams may pass through an adjustable delay line 114. This delay line can compensate for any path length differences between the origins of the beams within the laser source by extending the path of the one beam to match the path length of the other. The delay line may consist of two or more mirrors on a translation mechanism. The motion of the translation mechanism can be automated to optimize the probe response as discussed later.

The output beams of the laser source may be adjusted with a wavelength controller 112. The wavelength controller selects two beam frequencies $\sigma_1$ and $\sigma_2$ such that the difference $\Delta\sigma=\sigma_1-\sigma_2$ (or $\sigma_2-\sigma_1$) corresponds to a vibrational frequency in a Raman region of interest, typically in the mid-infrared. For example, in one embodiment the lasers can be selected to provide a tuning range of at least 900-1850 cm$^{-1}$. In another embodiment the laser source can be chosen to cover a tuning range of greater than 500-3600 cm$^{-1}$. In another embodiment, the laser source can be chosen to cover a tuning range from 0-24323 cm$^{-1}$. Such tuning ranges are necessary to cover the IR spectral regions of interest identified by bulk techniques such as FTIR or conventional confocal Raman spectroscopy. Once the two beams at frequencies $\sigma_1$ and $\sigma_2$ are arranged to be focused at a region in the vicinity of the AFM tip, the system can then be used to enable Raman measurements of sub-micron regions of the sample. The system can for example measure both local Raman spectra 124 and also create spatially resolved maps 126 of Raman contrast, corresponding to maps of chemical species on the sample. To accomplish these tasks, the system measures a probe response as a function of the Raman shift (the difference frequency $\Delta\sigma$) and/or the probe response as a function of relative tip-sample position. It is also possible under the current invention to perform hyperspectral imaging where a full Raman spectrum is collected at a plurality of tip-sample positions. From the hyperspectral "image cube," individual spectra can be selected for any desired tip-sample position and spatially resolved maps can be created for any Raman shift, i.e., wavenumber difference.

The probe response can comprise many different measurements. In a preferred embodiment, the probe response is the transient response resulting from the heating of a region of the sample due to the absorption of IR energy at Raman frequency $\Delta\sigma$, analogous to PTIR. In the case of absorption of a photon at function of the pump frequency of $\sigma_1$ and emission of a photon at the Stokes frequency of $\sigma_2$, the difference in energy between the two photons is absorbed by the sample as heat. If a pulsed source is employed with a high peak intensity, the absorbed heat may cause a significant temperature rise in the absorbing region of the sample. This temperature rise, as will be discussed later, can be optimized to be in the range of several degrees C. This temperature rise can lead to a rapid thermal expansion of the absorbing region of the sample. The rapid thermal expansion can create an easily detectable transient response in the cantilever, as discussed in U.S. Pat. No. 8,001,830 which is incorporated by reference.

In one embodiment the probe response is related to the motion of the cantilever in response to the energy absorbed by the sample. In an alternate embodiment the probe response is a temperature increase in a region of the cantilever probe. In the case of measuring the cantilever motion, a cantilever detection system is employed to measure a signal indicative of the motion of the cantilever. In the most common form, the cantilever motion is measured using an optical lever technique in which a laser beam 119 is directed towards the cantilever 100 and the reflected beam 121 is directed to a position sensitive detector 120. Many variations of this technique are known in the art, discussed in the incorporated references and thus will not be discussed in detail here. The cantilever motion can also be measured using optical interferometry, and a variety of non optical techniques including capacitive sensing, piezoelectric, piezoresistive and thermal dissipation techniques to name a few. (Thermal dissipation techniques have recently been shown by the group of William King with better sensitivity than many piezoresistive measurements.) Any mechanism that can measure cantilever motion with roughly nanometer sensitivity can be sufficient. Alternately, temperature sensing probes may be used to directly monitor the heat generated in the vicinity of the AFM tip.

Once a probe response is recorded, it may be optionally demodulated using demodulator 122. The demodulator may be a fast Fourier transform (FFT), a lock-in amplifier, an RMS detector, filtering electronics or other device used to select a probe response over a desired frequency range. The demodulator may comprise analog electronics, digital electronics, digital computation and any combination of these. The demodulator may produce one of more signals indicative of the probe response to the energy absorbed by the sample. For example it may produce signals including peak deflection, oscillation amplitude, phase, amplitude at one or more frequencies, integrated amplitude over a selected frequency region, or other signals. The demodulator can measure the probe response at one or more of the frequencies supplied by the modulation control 118 or at a heterodyne frequency resulting from nonlinear mixing of two or more of the modulation signals as described in the copending incorporated reference Multiple Modulation Heterodyne Force Microscopy.

The output of the demodulator can be plotted as a function of the Raman shift (the difference frequency $\Delta\sigma$) to create a Raman spectrum 124 of a sub-micron region of the sample. It is also extremely interesting to perform spatially resolved Raman measurements. To do this the system can plot the probe response as a function of relative tip-sample position. To achieve this, the probe response is measured and plotted at a plurality of tip-sample positions.

To measure at a plurality of tip-sample positions, relative motion can be generated between the tip 102 and sample 104 with a scanner 108. The scanner can be a single mechanism that moves in three axes or any combination of single or dual axis translation mechanisms. The scanner can achieve relative tip-sample motion by moving the probe tip, the sample or any combination of the two. In a preferred embodiment the scanner translates the sample while the probe is held in a fixed position relative to the incoming laser beams.

Figure 2:
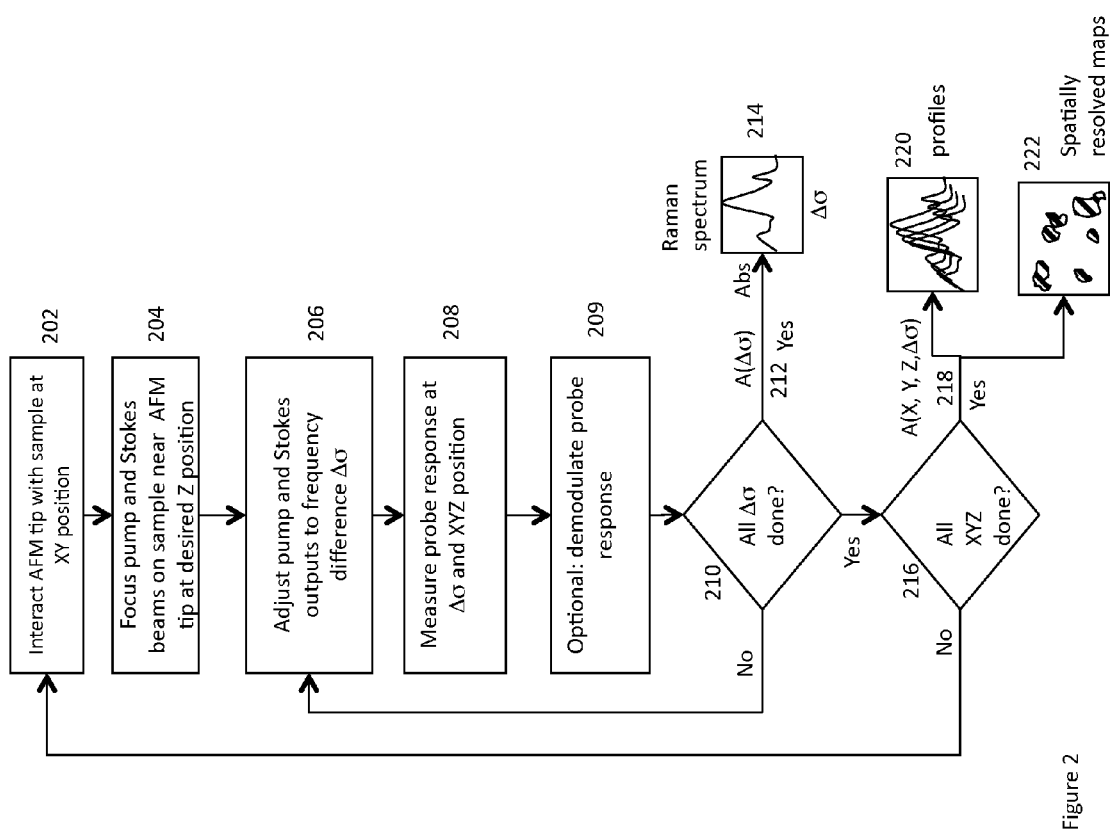
FIG. 2 is a flow chart of an embodiment of the invention.

FIG. 2 shows a simplified schematic diagram of a method under the current invention. As mentioned in the description accompanying FIG. 1, a probe tip of an AFM is interacted with a sample at a desired XY position (step 202). Two laser beams are focused on a region of the sample near the AFM tip (step 204). The two laser beams are in one embodiment originate from one or more pulsed laser sources and they pulses are arranged to arrive at the sample at substantially the same time, or at least with a temporal overlap. The optical frequency (or equivalently wavelengths) of one or both of the laser beams are adjusted to give a frequency difference of $\Delta\sigma$ (step 206). The frequency difference $\Delta\sigma$, also called the Raman shift can be selected to be within the mid-IR wavelength range, for example 900-1850 cm$^{-1}$ (which covers important bands like CH, amide and carbonyl bands, for example) or 500-3600 (which covers most mid-IR bands including the CH, NH, and OH bands in the 2800-3600 cm$^{-1}$ region). In general, it is preferable for the laser source(s) be able to support Raman shift frequency range of at least 1000 cm$^{-1}$ to allow measurements and comparison of absorptions of at least two or more distinct vibration bands.

Once a Raman shift $\Delta\sigma$ is selected, the probe response is measured for that $\Delta\sigma$ and XY sample position (step 208). It is also possible to adjust the focus of the laser beam below the surface to perform depth profiling, i.e., measuring the probe response at a plurality of z-positions (depth). The raw probe response measurement can optionally be demodulated (step 209) to enhance the signal-to-noise and/or sensitivity. The demodulation process, as described previously, can use any number of frequency selective and/or noise reduction techniques to extract a signal indicative of the heat absorbed by the sample in response to the absorption of IR energy from the stimulated Raman illumination. The measurements are repeated at a plurality of Raman shifts $\Delta\sigma$ and/or XYZ positions (see decision blocks 210 and 216). Once measurements at all desired Raman shifts $\Delta\sigma$ are complete, the probe response A as a function of $\Delta\sigma$ (212) can be plotted to form a Raman spectrum of a sub-micron region of the sample. This probe response can be also analyzed as a function of XY and/or Z position on the sample (218) to create spatially resolved maps and profiles.

Laser Sources

This section describes a variety of laser sources that can be used with the current invention. In a preferred embodiment, a nanosecond optical parametric oscillator (OPO) can be used. For example, Ekspla manufactures a model NT242 that is pumped at 355 nm wavelength and is tunable from 210 to 2600 nm. Using the 355 nm beam as the pump, and using the OPO output as the Stokes beam, this provides a tuning range $\Delta\sigma$ of 0 to 24323 cm$^{-1}$, far exceeding the range of conventional Raman spectrometers. If we focus on an interesting range of Raman absorptions, for example 500 cm$^{-1}$ to 3600 cm$^{-1}$, using the 355 nm pump would only require an OPO that tunes from 361 nm to 407 nm. In this wavelength region where the laser can use sum frequency or second harmonic generation, the output pulse energy can be more than 20 uJ, which can create detectable thermal expansion of sample. This laser also supports pulse repetition rates of 1000 kHz that provides for rapid and efficient co-averaging of the cantilever response to the absorbed radiation. For even higher power levels, Ekspla manufactures a flash lamp pumped laser (NT340 series) with pulse energies in the mJ range. Opotek also makes flashlamp and diode pumped OPO's with suitable tuning ranges. Alternate laser sources could include picosecond tunable lasers, for example the Toptica iChrome TVIS which is tunable from 488 to 640 nm. Using a pump at 488 nm, this would enable tuning from 0-4867 cm$^{-1}$. While the pulse energy is much smaller than the Ekspla system, the short pulse duration and much higher repetition rate (~40 MHz) can still lead to a detectable thermal signal. Other suitable lasers are available from other vendors. In the case of the use of two separate laser sources it is desirable to synchronize the emission from the two laser sources such that the pulses at the two different wavelengths arrive at the region of the interest on the sample at substantially the same time. It can also be advantageous to pulse the lasers synchronized with the oscillation of the cantilever to gain continuous resonant enhancement of from the AFM cantilever.

Temperature Increase

Yakovlev et al have recently reported on stimulated Raman photoacoustic imaging (PNAS Nov. 23, 2010 vol. 107 no. 47 20335-20339, DOI: 10.1073/pnas.1012432107). In this publication they used two laser beam system to stimulated Raman absorption and detected the increase in local heating with in the far field with an ultrasonic detector. This paper includes calculations of temperature increase associated with a stimulated Raman process. In the paper, they estimate temperature increases of order 60 mK, near the detection limit of PTIR technique. We will show below, however, that it is possible to achieve temperature increases of many tens of Kelvin, easily within the PTIR detection limit. The Yakolev publication reports the following equation for the temperature rise $\Delta T$ associated with absorbing IR energy from stimulated Raman laser pulses:

$$\Delta T = \frac{N_A}{M c_v} \frac{\lambda_s^4}{2\hbar\pi^2 c^2} \frac{d\sigma}{d\Omega} \frac{\omega_{vib}}{\Gamma} I_p I_s \tau_p$$

Where $N_A$ is Avagadro's number, M is the molecular weight of the absorbing molecules, $c_v$ is the sample heat capacity, $\lambda_s$ is the wavelength of the Stokes beam, h is the reduced Planck's constant, $d\sigma/d\Omega$ is the differential scattering cross section for spontaneous Raman emission, $\omega_{vib}$ is the Raman absorbing frequency (equivalent to the term $\Delta\sigma$ used elsewhere in this specification), $\Gamma$ is the Raman linewidth, $I_p$ and $I_s$ are the peak intensities of the pump and Stokes beams respectively, and $\tau_p$ is the laser pulse time. Using typical values for chloroform molecules and conditions used in their experiments, Yakovlev calculates a temperature increase of 0.06 K. For Stimulated Raman AFM, we desire a higher temperature increase to lead to a more easily detectable thermal expansion.

The invention requires a novel approach to achieve measurable sample expansion or measurable temperature shifts as contrasted to that of earlier works such as Wickramasinghe. First, we note that dramatic signal increases can be achieved by focusing the laser to diffraction limited spots. If the pump and Stokes beams have similar intensities $I_p=I_s=I_0$ the temperature increase goes like $I_0^2$. The laser intensity $I_0$ in turn goes like $1/r^2$, where r is the focused beam radius. So the temperature rise goes like the $1/r^4$. The Yakovlev paper cites a 50 um diameter laser spot. Using a diffraction limited spot in the ultraviolet with a spot diameter ~0.25 μm (for example using 0.9 NA UV at 355 nm wavelength), would provide the opportunity for a signal increase of $(50/0.25)^4=1.6\times10^9$. This would obviously create heating that would exceed the damage threshold of the sample, but more moderate temperature improvements are readily available by adjusting other parameters. For example, using a spot diameter of around 0.5 μm, pulse energies of 1 μJ, and pulse durations around 70 nsec would provide an estimated temperature rise of around 30K, assuming a differential cross section $d\sigma/d\Omega$ of around $10^{-34}$ m$^2$, a heat capacity $c_v=10^3$ J/(kg K), and a molar mass M of around 0.1 kg/mol. Note that for this calculation, product ($\lambda_s^4$ $d\sigma/d\Omega$) is assumed constant since $d\sigma/d\Omega$ is known to scale like $1/\lambda_s^4$. Note that there are also potentially orders of magnitude of dynamic range for this measurement. If the differential Raman cross section is much smaller, say around $10^{-36}$ m$^2$, a temperature increase of 30K can still be achieved by focusing the laser beam to a diffraction limited spot (~0.25 μm diameter) and increasing the laser pulse energies to 2.5 μJ. Since the detected thermal signal heat goes like the product of the pump pulse energy and the Stokes pulse energy, very high enhancements are possible. For example, increasing pulse energies to 20 uJ for each beam over 1 μJ in the earlier example would boost the signal strength by 400×. Using pulse energies of 20 uJ and diffraction limited spots, it is possible generate 2K temperature rises from molecules with Raman scattering cross sections as low as $10^{-39}$ m$^2$. (In practice it is necessary to consider damage thresholds from the UV beams in addition to the heat generated from the Raman absorption.)

Spatial Resolution

Spatial resolution of this technique can be dramatically improved compared to conventional Raman spectroscopy. There are several reasons for this. First, the detection occurs in the extreme near field, directly at the point of absorption of the Raman photons. Conventional Raman spectroscopy is detected in the far field by optical detectors or in the case of photoacoustic measurements by an ultrasonic detector. In this case, the detection mechanisms are limited by optical diffraction limits. In the case of probe-based detection, the spatial resolution can be as fine as the probe radius since the local forces can be measured in the extreme near field. Spatial resolution can be compromised by thermal diffusion, but heterodyne techniques can be used to overcome these issues as described in the copending application 61/460,666 "Multiple Modulation Heterodyne Infrared Spectroscopy."

The current invention also has a significant advantage over prior AFM-based IR spectroscopy where the source is a tunable infrared laser, for example as described in the PTIR patent and copending applications, which is incorporated by reference. In the case of illumination with an IR beam the focused spot is much larger, usually on the scale of a few 10s of microns. This results in illumination of a large area of the sample and absorbing regions in the sample away from the tip can contribute to an unwanted background. In the current invention, the laser source can operate in the UV, visible, or near IR. In all cases the focus spot will be considerable smaller than the mid-IR spot mentioned previously. As such the area of the sample that can contribute to the background is much smaller. Additionally, the absorption of Raman photons through the stimulated Raman process occurs only when both pump and Stokes photons are incident on the same location and the intensity of the temperature signal is proportional to the product of the pump and Stokes beam intensities. There is the possibility for even further enhancement in spatial resolution by spatially offsetting the two laser beams such that their maxima do not fully overlap. In this case the Raman absorption can be confined to the region of greatest overlap, a region that can be smaller than the diffraction limited spot size of either beam.

Tip-Enhancement

A great deal of attention in recent years has been paid to the field of tip-enhance Raman spectroscopy. In this field a metal coated AFM tip is used to locally enhance the intensity of the excitation signal under the AFM tip, resulting in an enhancement in the Raman shifted light scattered into the far field. This same mechanism can be used to enhance the detected thermal signal. In fact, the enhancement of the electric fields by the AFM tip can have a fourth order enhancement. Assume the local electric fields of the pump and Stokes beams are enhanced by a tip-enhancement factor of $\alpha$. The new enhanced intensities $I_p$ and $I_s$ go like $(\alpha E_{p(s)})^2$. So the temperature increase $\Delta T$ will increase by a factor of $\alpha^4$, i.e. the $4^{th}$ power of the tip enhancement factor. This is a significant breakthrough as it enables use of tips with much more modest enhancement factors to achieve readily detectable signals. For example even a modest tip-enhancement factor of 6× in the electric field can provide a $6^4=1296×$ enhancement in the local temperature increase in the sample near the tip. This is significant because although much, much higher tip-enhancement factors have been reported in the literature, it has been difficult for commercial probe or instrument manufacturers to deliver the probes with consistently high enhancement factors to their customers. The $4^{th}$ power dependence of the temperature signal on the tip-enhancement factor allows probe manufacturers to supply probes that are much more easily manufacturable and much more consistent.

Integration with TERS and s-SNOM

It should be noted that the current invention can easily be integrated with conventional scattering scanning near field optical microscopy (s-SNOM), scanning near field infrared microscopy (SNIM) and/or Tip-Enhanced Raman Spectroscopy (TERS). In these cases light scattered from the region of tip-sample interaction is collected in the far field with a detector and/or spectrometer. The current invention can be integrated with any of these techniques. Specifically, the stimulated Raman process can dramatically enhance the amount of light detected in the TERS setup as the Stokes beam can enhance the scattering cross section by many orders of magnitude versus conventional spontaneous Raman emission.

I claim:

1. A method of operating a probe microscope to obtain a vibrational spectrum of a sub-micron region of sample using stimulated Raman excitation, the method comprising:
    a. illuminating a sample with at least two beams of radiation wherein the two beams have a wavenumber difference of $\Delta\sigma$;
    b. interacting a tip of a probe microscope with a surface of the sample;
    c. measuring a probe response resulting from heating of the region of the sample due to absorption of energy at a wavenumber corresponding to $\Delta\sigma$;
    d. sweeping the wavenumber of at least one of the illuminating beams to measure the probe response as a function of wavenumber difference $\Delta\sigma$;
    e. Creating a vibrational spectrum of the region of the sample using the probe response as a function of wavenumber difference $\Delta\sigma$.

2. The method of claim 1 wherein at one of the beams of radiation is emitted from a laser source.

3. The method of claim 1 wherein at one of the beams of radiation is emitted from a pulsed laser source.

4. The method of claim 2 wherein the pulsed laser source is an optical parametric oscillator.

5. The method of claim 2 wherein the two beams originate from a single pump laser.

6. The method of claim 2 wherein pulses from the two beams are substantially temporally synchronized.

7. The method of claim 2 wherein there is at least a partial temporal overlap of the pulses from the two beams at the sample.

8. The method of claim 1 wherein the sweeping step sweeps the wavenumber difference $\Delta\sigma$ over a range of at least 1000 cm$^{-1}$.

9. The method of claim 1 wherein the sweeping step sweeps the wavenumber difference $\Delta\sigma$ over a range of at least 900-1850 cm$^{-1}$.

10. The method of claim 1 wherein the sweeping step sweeps the wavenumber difference $\Delta\sigma$ over a range of at least 500-3600 cm$^{-1}$.

11. The method of claim 3 where the pulsed laser source has a pulse duration of at least 1 picosecond.

12. The method of claim 11 where the pulse duration is at least 1 nanosecond.

13. The method of claim 3 where the pulsed laser source has a pulse repetition rate of at least 1 kHz.

14. A method of operating a probe microscope to obtain an image of a distribution of chemical species on a sample with sub-micron spatial resolution using stimulated Raman excitation, the method comprising:

a. illuminating a sample with at least two beams of radiation wherein the two beams have a wavenumber difference of $\Delta\sigma$;
b. interacting a tip of a probe microscope with a surface of the sample;
c. measuring a probe response resulting from heating of the region of the sample due to absorption of energy at a wavenumber corresponding to $\Delta\sigma$;
d. mapping the probe response at a plurality of locations on the sample.

15. A method of operating a probe microscope to obtain an image of a distribution of chemical species on a sample with sub-micron spatial resolution using stimulated Raman excitation, the method comprising:
a. illuminating a sample with at least two beams of radiation wherein the two beams have a wavenumber difference of $\Delta\sigma$;
b. interacting a tip of a probe microscope with a surface of the sample;
c. sweeping the wavenumber of at least one of the illuminating beams to measure the probe response as a function of wavenumber difference $\Delta\sigma$ where the sweeping is done over a range of at least 1000 cm$^{-1}$.

16. The method of claim 15 wherein at one of the beams of radiation is emitted from a laser source.

17. The method of claim 15 wherein at one of the beams of radiation is emitted from a pulsed laser source.

18. The method of claim 17 wherein the pulsed laser source is an optical parametric oscillator.

19. The method of claim 16 wherein the two beams originate from a single pump laser.

20. The method of claim 17 wherein pulses from the two beams are substantially temporally synchronized.

21. The method of claim 17 wherein there is at least a partial temporal overlap of the pulses from the two beams at the sample.

22. The method of claim 15 wherein the sweeping step sweeps the wavenumber difference $\Delta\sigma$ over a range of at least 900-1850 cm$^{-1}$.

23. The method of claim 15 wherein the sweeping step sweeps the wavenumber difference $\Delta\sigma$ over a range of at least 500-3600 cm$^{-1}$.

24. The method of claim 17 where the pulsed laser source has a pulse duration of at least 1 picosecond.

25. The method of claim 17 where the pulse duration is at least 1 nanosecond.

26. The method of claim 17 where the pulsed laser source has a pulse repetition rate of at least 1 kHz.

27. The method of claim 15 further comprising the step of sweeping the wavenumber of at least one of the illuminating beams to measure the probe response as a function of wavenumber difference to create a $\Delta\sigma$ hyperspectral image cube.

28. The method of claim 1 comprising focusing the two beams of radiation to two spots that overlap with the tip of the probe microscope, wherein the two focused spots are arranged to overlap each other only over a portion of the focused spots, thus reducing the area on the sample where stimulated Raman scattering occurs.

29. The method of claim 28 comprising adjusting the reduction of overlap of the two focused spots to provide improvement in spatial resolution of the vibration spectrum.

30. The method of claim 14 comprising focusing the two beams of radiation to two spots that overlap with the tip of the probe microscope, wherein the two focused spots are arranged to overlap each other only over a portion of the focused spots, thus reducing the area on the sample where stimulated Raman scattering occurs.

31. The method of claim 30 comprising adjusting the reduction of overlap of the two focused spots to provide improvement in spatial resolution of the vibration spectrum.

* * * * *